United States Patent
Song et al.

(10) Patent No.: US 10,867,384 B2
(45) Date of Patent: Dec. 15, 2020

(54) SYSTEM AND METHOD FOR AUTOMATICALLY DETECTING A TARGET OBJECT FROM A 3D IMAGE

(71) Applicant: SHENZHEN KEYA MEDICAL TECHNOLOGY CORPORATION, Shenzhen (CN)

(72) Inventors: Qi Song, Seattle, WA (US); Shanhui Sun, Princeton, NJ (US); Hanbo Chen, Seattle, WA (US); Junjie Bai, Seattle, WA (US); Feng Gao, Seattle, WA (US); Youbing Yin, Kenmore, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 78 days.

(21) Appl. No.: 15/996,434

(22) Filed: Jun. 2, 2018

(65) Prior Publication Data
US 2019/0050981 A1 Feb. 14, 2019

Related U.S. Application Data

(60) Provisional application No. 62/542,890, filed on Aug. 9, 2017.

(51) Int. Cl.
*G06K 9/62* (2006.01)
*G06T 7/00* (2017.01)
(Continued)

(52) U.S. Cl.
CPC .......... *G06T 7/0012* (2013.01); *A61B 5/0037* (2013.01); *A61B 5/7264* (2013.01);
(Continued)

(58) Field of Classification Search
CPC ...... G06K 9/00; G06K 9/3233; G06K 9/3241; G06K 9/34; G06K 2209/05;
(Continued)

(56) References Cited

U.S. PATENT DOCUMENTS 9,589,374 B1 * 3/2017 Gao ...................... G06T 7/0012
10,410,096 B2 * 9/2019 Dijkman .................. G06K 9/66
(Continued)

OTHER PUBLICATIONS

Shuran Song and Jianxiong Xiao, "Deep Sliding Shapes for Amodal 3D Object Detection in RGB-D Images", IEEE, 2016 IEEE Conference on Computer Vision and Pattern Recognition (CVPR), Jun. 2016, pp. 808-816 (Year: 2016).*

(Continued)

*Primary Examiner* — Eric Rush
(74) *Attorney, Agent, or Firm* — Bayes PLLC

(57) ABSTRACT

A computer-implemented method for automatically detecting a target object from a 3D image is disclosed. The method may include receiving the 3D image acquired by an imaging device. The method may further include detecting, by a processor, a plurality of bounding boxes as containing the target object using a 3D learning network. The learning network may be trained to generate a plurality of feature maps of varying scales based on the 3D image. The method may also include determining, by the processor, a set of parameters identifying each detected bounding box using the 3D learning network, and locating, by the processor, the target object based on the set of parameters.

20 Claims, 10 Drawing Sheets

(51) Int. Cl.

| | | |
|---|---|---|
| *G06T 7/11* | (2017.01) | |
| *G06N 3/04* | (2006.01) | |
| *G06N 5/04* | (2006.01) | |
| *G16H 30/40* | (2018.01) | |
| *G06T 11/20* | (2006.01) | |
| *G06N 20/00* | (2019.01) | |
| *G06T 7/73* | (2017.01) | |
| *G06N 3/08* | (2006.01) | |
| *G16H 50/70* | (2018.01) | |
| *G06K 9/32* | (2006.01) | |
| *A61B 5/00* | (2006.01) | |
| *G06N 3/063* | (2006.01) | |

(52) U.S. Cl.
CPC .......... *A61B 5/7267* (2013.01); *G06K 9/3233* (2013.01); *G06K 9/3241* (2013.01); *G06N 3/04* (2013.01); *G06N 3/0454* (2013.01); *G06N 3/08* (2013.01); *G06N 5/046* (2013.01); *G06N 20/00* (2019.01); *G06T 7/11* (2017.01); *G06T 7/73* (2017.01); *G06T 11/20* (2013.01); *G16H 30/40* (2018.01); *G16H 50/70* (2018.01); *G06K 2209/053* (2013.01); *G06K 2209/21* (2013.01); *G06N 3/063* (2013.01); *G06T 2207/10081* (2013.01); *G06T 2207/20081* (2013.01); *G06T 2207/30064* (2013.01); *G06T 2210/12* (2013.01)

(58) Field of Classification Search
CPC .......... G06K 2209/053; G06K 2209/21; G06T 7/0012; G06T 7/10; G06T 7/11; G06T 7/70; G06T 7/73; G06T 11/20; G06T 2207/10021; G06T 2207/10028; G06T 2207/10072; G06T 2207/10081; G06T 2207/10036; G06T 2207/20016; G06T 2207/20021; G06T 2207/20081; G06T 2207/20084; G06T 2207/30004; G06T 2207/30061; G06T 2207/30064; G06T 2207/30096; G06T 2210/12; G06N 3/04; G06N 3/0454; G06N 3/063; G06N 3/08; G06N 5/046; G06N 5/047; G06N 20/00; G16H 30/40; G16H 50/20; G16H 50/70; A61B 5/0037; A61B 5/7264; A61B 5/7267; A61B 6/12; A61B 6/52; A61B 6/5211
USPC ....... 382/100, 103, 128, 131, 154–158, 181, 382/195, 224, 282, 291; 600/407, 408; 128/920, 922–925; 706/12, 15, 20, 26, 706/27
See application file for complete search history.

(56) References Cited

U.S. PATENT DOCUMENTS

| | | | | |
|---|---|---|---|---|
| 10,453,200 | B2* | 10/2019 | Mukherjee | G06T 7/12 |
| 10,467,459 | B2* | 11/2019 | Chen | G06K 9/00281 |
| 10,621,725 | B2* | 4/2020 | Fan | G06K 9/00818 |
| 2013/0259345 | A1* | 10/2013 | El-Baz | G06T 7/0012 |
| | | | | 382/131 |
| 2015/0254842 | A1* | 9/2015 | Brown | G06T 7/0012 |
| | | | | 382/131 |
| 2016/0174902 | A1* | 6/2016 | Georgescu | G06T 7/73 |
| | | | | 600/408 |
| 2017/0046616 | A1* | 2/2017 | Socher | G06K 9/4628 |
| 2017/0124415 | A1* | 5/2017 | Choi | G06K 9/628 |
| 2017/0147905 | A1* | 5/2017 | Huang | G06K 9/6232 |
| 2017/0200067 | A1* | 7/2017 | Zhou | G06T 7/143 |
| 2017/0287137 | A1* | 10/2017 | Lin | G06K 9/66 |
| 2018/0039853 | A1* | 2/2018 | Liu | G06K 9/72 |
| 2018/0061059 | A1* | 3/2018 | Xu | G06N 3/04 |
| 2018/0137642 | A1* | 5/2018 | Malisiewicz | G06T 7/11 |
| 2018/0165808 | A1* | 6/2018 | Bagci | G06T 7/00 |
| 2018/0253622 | A1* | 9/2018 | Chen | G06K 9/627 |
| 2018/0315188 | A1* | 11/2018 | Tegzes | G06K 9/2054 |

OTHER PUBLICATIONS

Tsung-Yi Lin, Piotr Dollár, Ross Firshick, Kaiming He, Bharath Hariharan, and Serge Belongie, "Feature Pyramid Networks for Object Detection", IEEE, 2017 IEEE Conference on Computer Vision and Pattern Recognition (CVPR), Jul. 2017, pp. 936-944 (Year: 2017).*

Shu Liu, Xiaojuan Qi, Jianping Shi, Hong Zhang and Jiaya Jia, "Multi-scale Patch Aggregation (MPA) for Simultaneous Detection and Segmentation", IEEE, 2016 IEEE Conference on Computer Vision and Pattern Recognition (CVPR), Jun. 2016, pp. 3141-3149 (Year: 2016).*

Long, Jonathan et al., "Fully Convolutional Networks for Semantic Segmentation", UC Berkeley, @cs.berkeley.edu, CVPR 2014, 10 pages.

Girshick, Ross et al., "Rich feature hierarchies for accurate objec6t detection and semantic segmentation", Tech report, UC Berkeley and ICSI, @eecs.berkeley.edu, CVPR 2014, 11 pages.

Sun, Shanhui et al., "Automated 3-D Segmentation of Lungs With Lung Cancer in CT Data Using a Novel Robust Active Shape Model Approach", IEEE Transaction on Medical Imaging, vol. 31, No. 2, Feb. 2012, pp. 449-460.

He, Kaiming et al., "Mask R-CNN", Technical Report, Facebook AI Research (FAIR), arXiv:1703.06870v3 [cs.CV] Jan. 24, 2018, 12 pages.

Ren, Shaoqing et al., "Faster R-CNN: Towards Real-Time Object Detection with Region Proposal Networks", NIPS 2015, arXiv:1506.01497v3 [cs.CV] Jan. 6, 2016, 14 pages.

Simonyan, Karen et al., "Very Deep Convolutional Networks for Large-Scale Image Recognition", Published as a conference paper at ICLR 2015, Visual Geometry Group, Department of Engineering Science, University of Oxford, @robots.ox.ac.uk, arXiv:1409.1556v6 [cs.CV] Apr. 10, 2015, 14 pages.

Ronneberger, Olaf et al., "U-Net Convolutional Networks for Biomedical Image Segmentation", Computer Science Department and BIOSS Centre for Biological Signalling Studies, University of Freiburg, Germany, MICCAI 2015, ronneber@informatik.uni-freiburg.de, http://lmb.informatik.uni-freiburg.de, arXiv:1505.04597v1 [cs.CV] May 18, 2015, 8 pages.

Girshick, Ross et al., "Fast R-CNN", Microsoft Research, rbg@microsoft.com, ICCV 2015, arXiv:1504.08083v2 [cs.CV] Sep. 27, 2015, 9 pages.

First Office action issued in related Chinese Application No. 201810789942.0, dated Apr. 29, 2020, 9 pages.

"Deep Sliding Shapes for Amodal 3D Object Detection in RGB-D Images", Shuran Song et al. 2016 IEEE Conference on Computer Vision and Pattern Recognition, 9 pages.

"Feature Pyramid Network for Object Detection", Tsung-Yi Lin et al. 2017 IEEE Conference on Computer Vision and Pattern Recognition, 9 pages.

* cited by examiner

SYSTEM AND METHOD FOR AUTOMATICALLY DETECTING A TARGET OBJECT FROM A 3D IMAGE

CROSS-REFERENCE TO RELATED APPLICATION

This application claims the benefit of priority to U.S. Provisional Application No. 62/542,890, filed on Aug. 9, 2017, the entire contents of which are incorporated herein by reference.

TECHNICAL FIELD

The disclosure generally relates to image processing and analysis. More specifically, this disclosure relates to method and system for automatically locating and detecting a target object from a 3D image.

BACKGROUND

The accuracy of diagnosis and outcome of treatment depend on the quality of medical image analysis, especially detection of target object (such as organ, tissue, target site, etc.,). Volumetric (3D) imaging, such as volumetric CT, captures more valuable medical information compared to conventional two-dimensional imaging, and thus facilitates more accurate diagnoses. However, usually the target object is detected by experienced medical personnel such as radiologists instead of machines, which makes it tedious, time consuming and error prone.

One example is detecting a lung nodule from a pulmonary image. FIG. 1 shows an example of an axial image from a volumetric chest CT. The high-density mass inside a white bounding box corresponds to a lung nodule. In order to detect such a lung nodule, radiologists have to screen hundreds and thousands of images from volumetric CT scans. Identifying nodules merely from 2D images is not a trivial task due to lack of 3D spatial information. It is not easy to differentiate between small nodules and vessels in 2D images because vessels in 2D axial views are also round or elliptical, which look like nodules. Usually, radiologists need to examine neighboring images to reconstruct 3D spatial relationship virtually and/or examine sagittal or coronal views (a lower resolution) for reference. Detecting a lung nodule thus rely entirely on the radiologist's experience.

Although some basic machine learning methods are introduced for the detection, these methods usually define features artificially, and as a result the detection accuracy is low. Besides, such machine learning is usually limited to 2D image learning, but cannot detect a target object directly in a 3D image due to lack of 3D spatial information and the substantial computation resource needed for 3D learning.

This disclosure provides a method and system that can quickly, accurately, and automatically detect a target object from a 3D image by means of a 3D learning network. Such detection may include but not limited to locating the target object, determining the size of the target object, and identifying the type of the target object (e.g. a vessel or a lung nodule).

SUMMARY

In one aspect, the present disclosure is directed a computer-implemented method for automatically detecting a target object from a 3D image is disclosed. The method may include receiving the 3D image acquired by an imaging device. The method may further include detecting, by a processor, a plurality of bounding boxes as containing the target object using a 3D learning network. The learning network may be trained to generate a plurality of feature maps of varying scales based on the 3D image. The method may also include determining, by the processor, a set of parameters identifying each detected bounding box using the 3D learning network, and locating, by the processor, the target object based on the set of parameters.

In another aspect, the present disclosure is further directed to a system for automatically detecting a target object from a 3D image. The system may include an interface configured to receive the 3D image acquired by an imaging device. The system may further include a processor that is configured to detect a plurality of bounding boxes as containing the target object using a 3D learning network. The learning network may be trained to generate a plurality of feature maps of varying scales based on the 3D image. The processor may be further configured to determine a set of parameters identifying each identified bounding box using the 3D learning network, and locate the target object based on the set of parameters.

In yet another aspect, the present disclosure is also directed to a non-transitory computer readable medium having instructions stored thereon. The instructions, when executed by a processor, may perform a method for automatically detecting a target object from a 3D image. The method may include receiving the 3D image acquired by an imaging device. The method may further include detecting a plurality of bounding boxes as containing the target object using a 3D learning network. The learning network may be trained to generate a plurality of feature maps of varying scales based on the 3D image. The method may also include determining a set of parameters identifying each detected bounding box using the 3D learning network, and locating the target object based on the set of parameters.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, system, or non-transitory computer readable medium having instructions thereon for implementing the method.

DETAILED DESCRIPTION

The term "target object" used herein may refer to any anatomical structure in the subject body, such as a tissue, a part of an organ, or a target site. For example, a target object may be a lung nodule.

Figure 1:
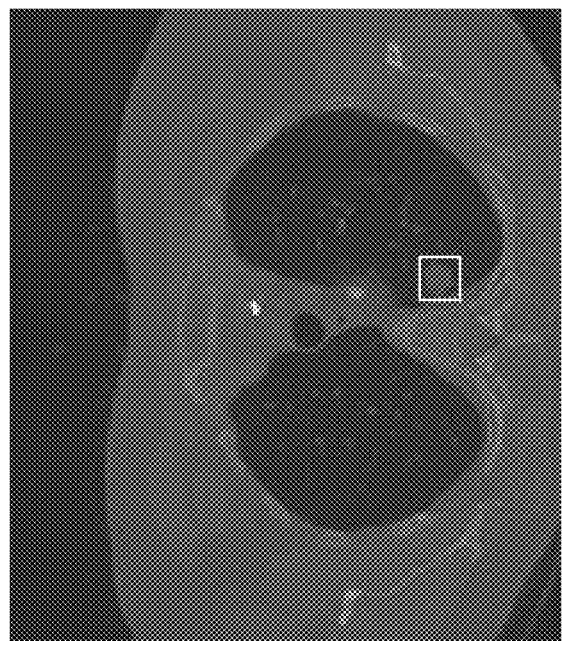
FIG. 1 illustrates an exemplary axial image generated by a volumetric chest computerized tomography.
Figure 2:
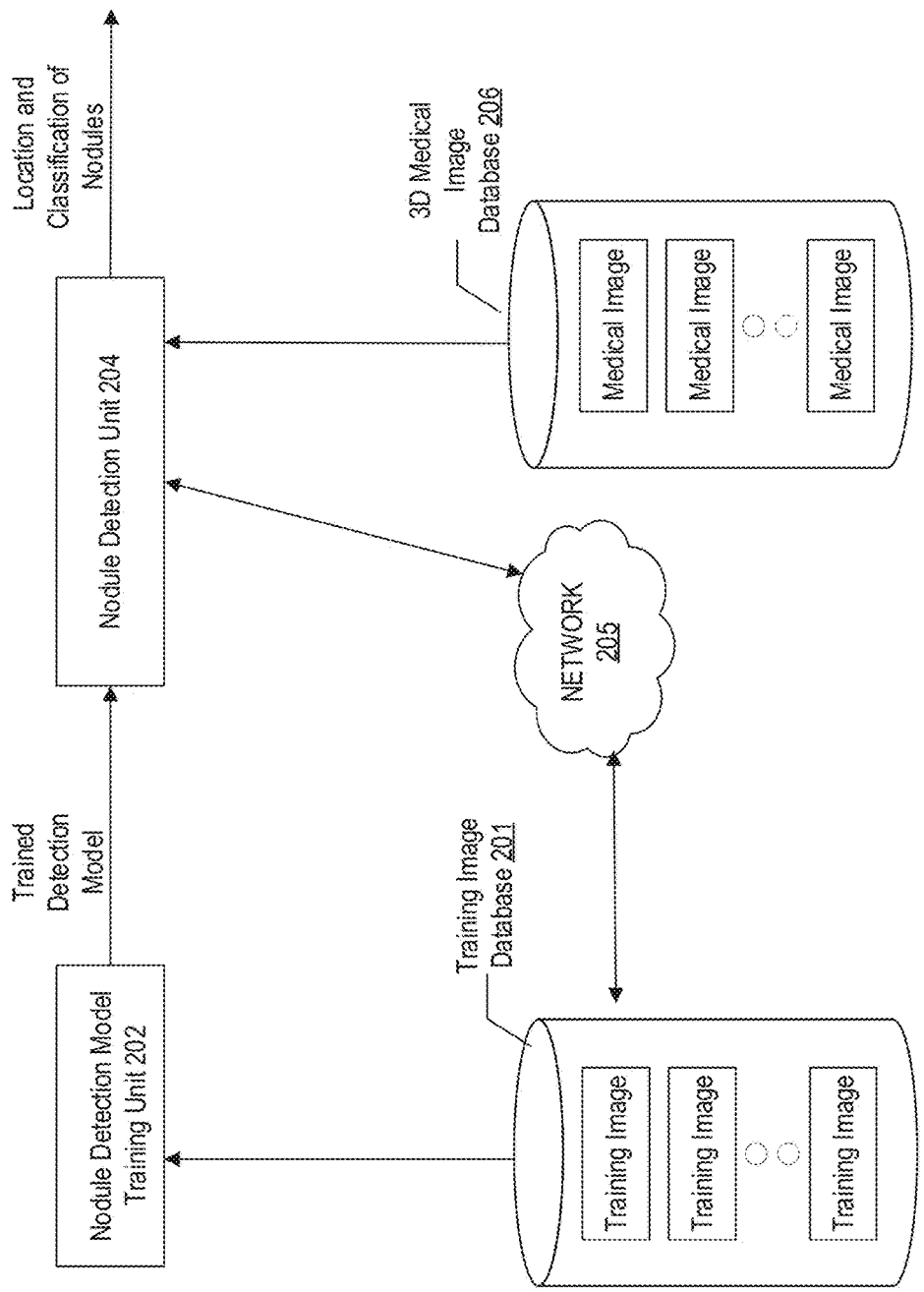
FIG. 2 illustrates an exemplary nodule detection system according to an embodiment of present disclosure.

FIG. 2 illustrates an exemplary nodule detection system 200 for automatically detecting a target object from a 3D image according to an embodiment of present disclosure. In this embodiment, a lung nodule is a target object. A lung nodule may become a target site for a treatment such as radiotherapy treatment. As shown in FIG. 2, the nodule detection system 200 includes: a nodule detection model training unit 202 for training a detection model; and a nodule detection unit 204 for detecting the location and classification of nodule objects using the trained detection model. The trained detection model may be transmitted from the nodule detection model training unit 202 to the nodule detection unit 204 so that the nodule detection unit 204 may obtain the trained detection model and apply it to the 3D medical images acquired, for example, from 3D medical image database 206. In some embodiments, the detection model may be a 3D learning network.

For example, the location of a nodule object may be identified by the center of the nodule object and its range. The classification of nodule object may be identified by a label selected out of (n+1) nodule labels, such as but not limited to non-nodule, first size of nodule, . . . , the nth size of nodule, as needed. For another example, the location may include a plurality of bounding boxes as containing the nodule objects. Alternatively or additionally, the location of a nodule object may include a set of parameters identifying each detected bounding box. The set of parameters may include coordinates identifying a position (e.g., center) of each bounding box in the 3D medical image. The set of parameters may further include dimensions identifying a size of each bounding box in the 3D medical image. On the basis of the detected bounding boxes and/or the set of parameters identifying the same, the nodule object may be located.

The training samples may be stored in a training image database 201, and may be acquired by the nodule detection model training unit 202 to train the detection model. Each training sample includes the medical image and location and classification information of nodule objects in the corresponding medical image.

In some embodiments, the outcome of the nodule detection unit 204, including the location and classification of the nodule object, may be visualized using heat-map overlaid with the original medical 3D image, e.g. the original volumetric CT image. In some embodiments, the detection result may be transmitted to the training image database 201 through network 205, and added together with the corresponding image as an additional training sample. In this manner, the training image database 201 may be updated continuously by including new detection results. In some embodiments, the nodule detection model training unit 202 may train the detection model with the updated training samples periodically, to improve the detection accuracy of the trained detection model.

The 3D learning network may be implemented by various neural networks. In some embodiments, the 3D learning network may be a feed-forward 3D convolutional neural network. Such feed-forward 3D convolutional neural network, when applied to a pulmonary volumetric CT image, may generate a plurality of feature maps, with each feature map corresponding to a type of the nodule object, such as non-nodule, first size of nodule, . . . , the nth size of nodule. In some embodiments, each grid cell of a feature map may indicate the presence status of the corresponding type of the nodule object in the corresponding region of the pulmonary volumetric CT image. On the basis of the plurality of feature maps, a plurality of bounding boxes and scores for the presence status of nodule object in those bounding boxes are generated. For example, a score 1.0 may indicate the presence of the corresponding type of the nodule object in the bounding box, a score 0.0 may indicate the non-presence of the corresponding type of the nodule object in the bounding box, and a score between 0.0 and 1.0 may suggest the probability for the presence of the corresponding type of the nodule object in the bounding box. In some embodiments, the feed-forward 3D convolutional neural network may be followed by non-maximum suppression layer to produce the final detection results. As an option, on top of the 3D convolutional neural network there may be appended with auxiliary fully connection layer(s) or auxiliary fully convolutional layer(s) as detection layer(s). In some embodiments, the bounding box may be 3D and identified by a set of parameters. For example, it may be identified by the coordinates of the center of the bounding box (x, y, z) and the box sizes on x-axis, y-axis, and z-axis respectively (size_x, size_y, size_z). In some embodiments, the 3D convolutional neural network may be trained to perform a regression on the set of parameters, thus the outcome of the 3D convolutional neutral network may include the classification result of the nodule objects (the detected type of the nodule objects) and 6 regressed parameter values for the respective detected type of nodule objects.

In one embodiment, the feed-forward 3D convolutional neural network may include a base network, and feature map scale 1 may be derived from the base network. For example, the base network may include three convolution blocks and three detection layers fc1, fc2, and fc3, with each convolution block composed of two 3×3×3 convolution layers, a ReLU layer and a 2×2×2 max-pooling layer. Convolution layer 1 and convolution layer 2 in convolution block 1 have 64 feature maps, convolution layer 1 and convolution layer 2 in convolution block 2 have 128 feature maps, and convolution layer 1 and convolution layer 2 in convolution block 3 have 128 feature maps. In some embodiments, fc1, fc2, and fc3 may be auxiliary fully connected layers used for classification tasks. In one embodiment, fc1 has 512 neurons following ReLU layers of fc1, fc2 has 128 neurons following ReLU layers, and fc3 may have a number of neurons depending on the classification. For example, if the nodule objects are to be classified into 10 types (such as non-nodule, nodule of size 1, nodule of size 2, . . . , nodule of size 9), then the number of neurons in fc3 layer is 10.

Figure 3:
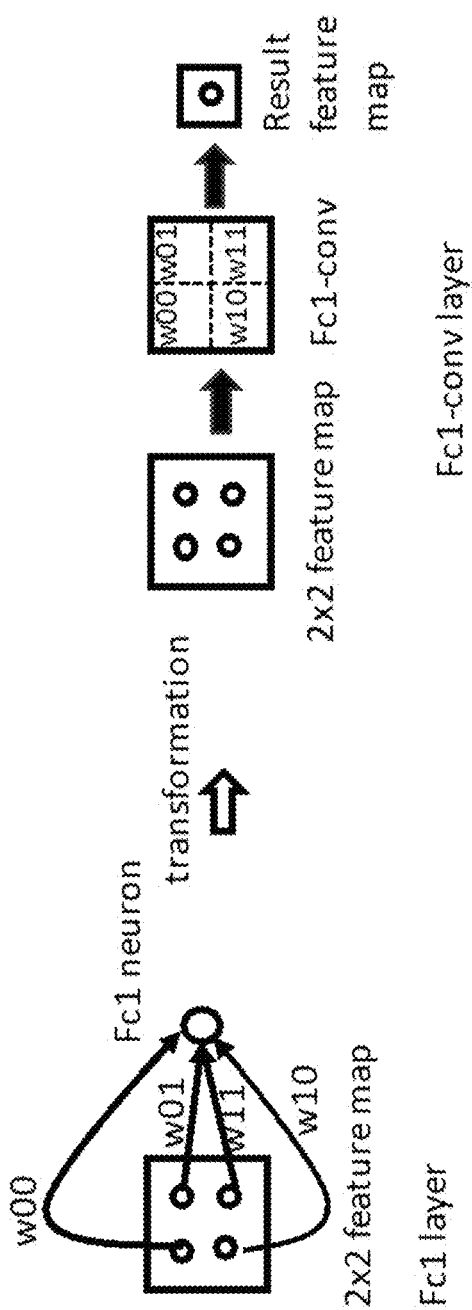
FIG. 3 illustrates an exemplary conversion from fully connected layers to fully convolution layers, according to an embodiment of present disclosure.

In another embodiment, the base network may be modified by transforming the above fully connected layers fc1, fc2, and fc3 to fully convolution layers Fc1-conv, Fc2-conv, and Fc3-conv, respectively. Accordingly, the calculation based on the modified base network may be accelerated due to the acceleration effect of convolution operation on the images. FIG. 3 illustrates an exemplary conversion from fully connected layers to fully convolution layers, according to an embodiment of present disclosure. In some embodiments, the kernel size of Fc1-cony may be the same as the size of the feature maps, which are pooled, if needed, after output from the convolution block 3, while Fc2-conv and Fc3-conv both have a kernel size of 1×1×1. In some embodiments, the number of feature maps of three fully convolution layers is the same as that of the corresponding fully connecting layers. As illustrated by FIG. 3, the weights of the convolutional kernels w00, w01, w10, and w11 are transformed from the corresponding weights w00, w01, w10, and w11 of the corresponding fully connected layers. In some embodiments, the fully connected layer's weights may be reshaped according to the convolutional kernel size and the number of the feature maps.

In an embodiment, the base network or its modified version described above may function as the 3D learning network to detect the bounding boxes directly. The base network may be applied on an input 3D image to generate a plurality of feature maps, with each feature map corresponding to a particular class of the object. In some embodiments, each grid cell of a feature map corresponds to a patch in the 3D image. For example, for the $i^{th}$ feature map corresponding to the $i^{th}$ class of the object, the value of its grid cell may indicate the probability that the $i^{th}$ class of the object exists in the corresponding patch of the 3D image. In some embodiments, the object within the patch may be classified based on the value of the corresponding grid cell of each feature map. Further, through transforming the coordinates of the grid cell from the feature map space to the 3D image space, initial bounding boxes may be generated with the classification result as its label. In some embodiments, for convolution operation without padding, the transformation may be performed using formula (1).

$$x_{ori} = \left\lfloor \frac{c_{1\_1}-1}{2} \right\rfloor + \left\lfloor \frac{c_{1\_2}-1}{2} \right\rfloor + \\ s_1 \cdot \left( s_2 \cdot \left( s_3 \cdot \left( x_f + \left\lfloor \frac{c_4-1}{2} \right\rfloor + \left\lfloor \frac{c_5-1}{2} \right\rfloor + \left\lfloor \frac{c_6-1}{2} \right\rfloor \right) \right) + \\ \left\lfloor \frac{c_{3\_1}-1}{2} \right\rfloor + \left\lfloor \frac{c_{3\_2}-1}{2} \right\rfloor \right) + \\ \left\lfloor \frac{c_{2\_1}-1}{2} \right\rfloor + \left\lfloor \frac{c_{2\_2}-1}{2} \right\rfloor \right)$$ formula (1)

wherein, $x_f$ is the coordinate in the prediction feature map, $x_{ori}$ is the coordinate in the image space, $s_1$, $s_2$, and $s_3$ are scale factors, $\lfloor \ \rfloor$ is a floor operation, $c_{i\_j}$ (i=1, 2, 3, j=1, 2) is the convolution kernel size of the $j^{th}$ convolutional layer in the $i^{th}$ convolutional block, $c_{1\_1}=c_{1\_2}=c_{2\_1}=c_{2\_2}=c_{3\_1}=c_{3\_2}=3$, $c_4=8$, $c_5=1$, $c_6=1$.

In some embodiments, for convolution operation with padding, the transformation may be performed using formula (2).

$$x_{ori} = s_1 \cdot \left( s_2 \cdot \left( s_3 \cdot \left( x_f + \left\lfloor \frac{c_4-1}{2} \right\rfloor + \left\lfloor \frac{c_5-1}{2} \right\rfloor + \left\lfloor \frac{c_6-1}{2} \right\rfloor \right) \right) \right)$$ formula (2)

In some embodiments, the 3D learning network may have multiple scales. For example, a multi-scale feature map based convolution network may be used. The number of scales may be determined based on different detection tasks. The multi-scale feature of the convolution network may be implemented in various ways. For example, the multiple feature maps may have the same scale size, but are obtained using different sizes of sliding windows. As another example, the feature maps may be down-sampled into different scales either using convolution filters or pooling filters or both, while the same size of sliding window is utilized. As yet another example, the feature maps may also be down-sampled into different scales using down-sampling layers, etc. Using the disclosed multi-scale feature map based convolution network may accelerate the calculation, thus making the 3D learning network based detection clinically applicable while capable of detecting object with a broad range of sizes.

In some embodiments, the 3D learning network, at each scale, produces a fixed number of detection results using a series of fully convolutional filters (also referred to as fully connected layers). In some embodiments, the 3D learning network may return a plurality of bounding boxes, each associated with two parts: object classification and a set of parameters identifying the corresponding bounding box. The object classification may have c classes. In one embodiment, c=3, where the three object types are non-lung background, non-nodule but lung tissues, and nodules, respectively. For the nodule class, the bounding boxes enclose the corresponding nodule objects. In some embodiments, a plurality of anchor boxes may be introduced for each feature map grid cell, so as to make the detected bounding box better track the target object. For example, the set of parameters identifying the corresponding bounding box may be regressed offsets relative to the corresponding anchor box on the coordinates (centered at the evaluated grid cell) and dimensions. For the nodule class, the offsets may be relative values (dx, dy, dz, dsize_x, dsize_y, and dsize_z) to the coordinates and dimensions of the corresponding anchor boxes. For each scale feature map, if k anchor boxes are associated with a grid cell of a feature map including s scales, a totally k*s bounding boxes (and k*s anchor boxes) are obtained for each grid cell. Then for each bounding box out of the k*s bounding boxes, a score for each class out of the c classes and its 6 offsets relative to the corresponding anchor box may be computed. This results in a total of (c+6)*k*s filters that are applied around each location in the feature maps. With the size of each feature map being m*n*d, (c+6)*k*s*m*n*d outputs may be produced. In some embodiments, the anchor boxes are 3D and associated with different scales of feature maps. In some embodiments, the anchor boxes may be scaled based on the scale of the corresponding feature map. Optionally, the location and size of the anchor boxes may be adapted by means of regression algorithm according to image information.

Figure 4:
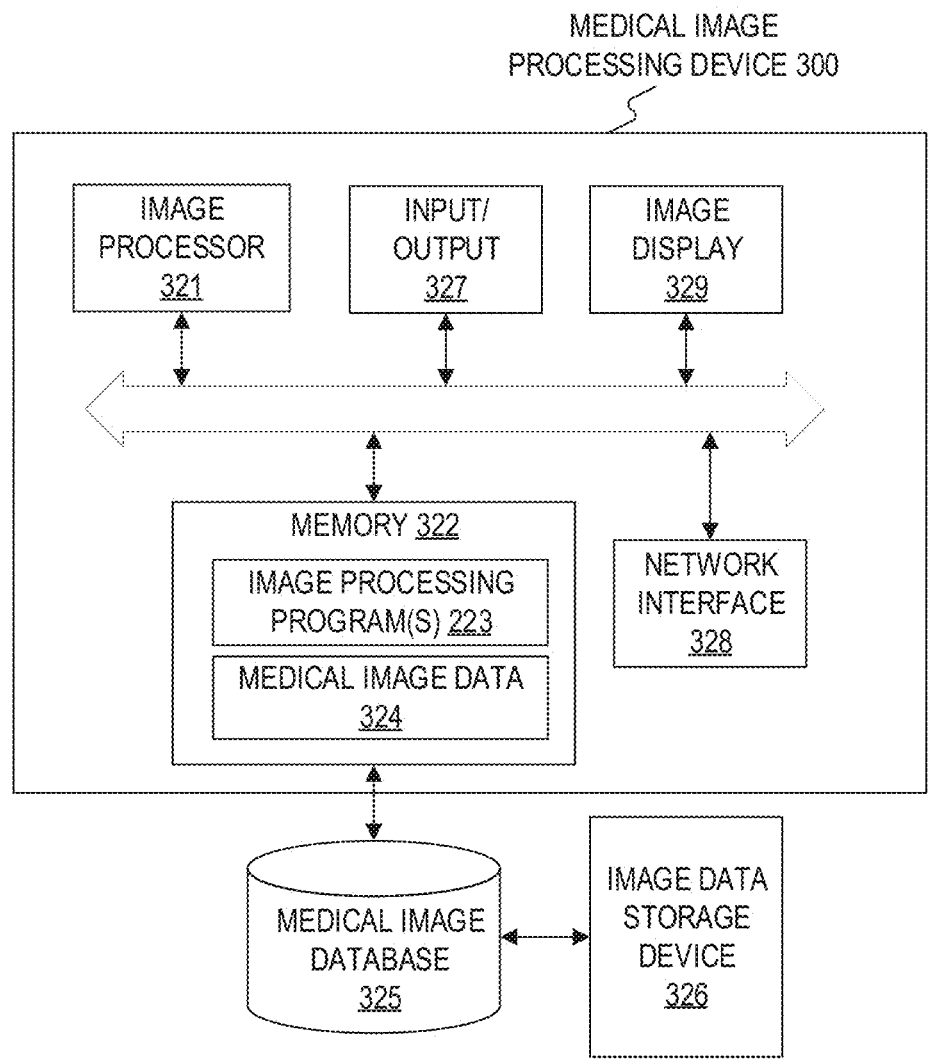
FIG. 4 depicts a block diagram illustrating an exemplary medical image processing device, according to an embodiment of present disclosure.

FIG. 4 depicts a block diagram illustrating an exemplary medical image processing device 300 adapted for automatically detecting a target object from a 3D image according to an embodiment of present disclosure. The medical image processing device 300 may include a network interface 328, by means of which the medical image processing device 300 may be connected to the network (not shown), such as but not limited to the local area network in the hospital or the Internet. The network can connect the medical image processing device 300 with external devices such as an image acquisition device (not shown), medical image database 325, an image data storage device 326. An image acquisition device may be any device that acquires images of an object, e.g. a DSA imaging device, an MRI imaging device, a CT image device, a PET imaging device, an ultrasound device, a fluoroscopic device, a SPECT imaging device, or other medical imaging device for obtaining medical images of the patient. For example, the imaging device may be a pulmonary CT imaging device, etc.

In some embodiments, the medical image processing device 300 may be a dedicated intelligent device or a general purpose intelligent device. For example, the device 300 may be a computer customized for image data acquisition and image data processing tasks, or a server placed in the cloud. For example, the device 300 may be integrated into the image acquisition device. Optionally, the device may include or cooperate with a 3D re-constructing unit for re-constructing the 3D image on the basis of the 2D images acquired by the image acquisition device.

The medical image processing device 300 may include an image processor 321 and a memory 322, and may additionally include at least one of an input/output 327 and an image display 329.

The image processor 321 may be a processing device that includes one or more general processing devices, such as a microprocessor, a central processing unit (CPU), a graphics processing unit (GPU), and the like. More specifically, the image processor 321 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 321 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 321 may be a special-purpose processor, rather than a general-purpose processor. The image processor 321 may include one or more known processing devices, such as a microprocessor from the Pentium™, Core™, Xeon™ or Itanium® family manufactured by Intel™, the Turion™, Athlon™, Sempron™, Opteron™ FX™, Phenom™ family manufactured by AMD™, or any of various processors manufactured by Sun Microsystems. The image processor 321 may also include graphical processing units such as a GPU from the GeForce®, Quadro®, Tesla® family manufactured by Nvidia™, GMA, Iris™ family manufactured by Intel™, or the Radeon™ family manufactured by AMD™. The image processor 321 may also include accelerated processing units such as the Desktop A-4 (6, 8) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to detect and localize a target object from a 3D image or to manipulate any other type of data consistent with the disclosed embodiments. In addition, the term "processor" or "image processor" may include more than one processor, for example, a multi-core design or a plurality of processors each having a multi-core design. The image processor 321 can execute sequences of computer program instructions, stored in memory 322, to perform various operations, processes, methods disclosed herein.

The image processor 321 may be communicatively coupled to the memory 322 and configured to execute computer-executable instructions stored therein. The memory 322 may include a read only memory (ROM), a flash memory, random access memory (RAM), a dynamic random-access memory (DRAM) such as synchronous DRAM (SDRAM) or Rambus DRAM, a static memory (e.g., flash memory, static random access memory), etc., on which computer executable instructions are stored in any format. In some embodiments, the memory 322 may store computer-executable instructions of one or more image processing program(s) 223. The computer program instructions can be accessed by the image processor 321, read from the ROM, or any other suitable memory location, and loaded in the RAM for execution by the image processor 321. For example, memory 322 may store one or more software applications. Software applications stored in the memory 322 may include, for example, an operating system (not shown) for common computer systems as well as for soft-controlled devices. Further, memory 322 may store an entire software application or only a part of a software application (e.g. the image processing program (s) 223) to be executable by the image processor 321. In addition, the memory 322 may store a plurality of software modules, for implementing the respective steps of the method for automatically detecting the target object from a 3D image or the process for training the 3D learning network consistent with the present disclosure. Besides, the memory 322 may store data generated/buffered when a computer program is executed, for example, medical image data 324, including the medical images transmitted from image acquisition device(s), medical image database 325, image data storage device 326, etc. Such medical image data 324 may include the received 3D medical image(s) for which the automatic detection of a target object is to be implemented. Besides, the medical image data 324 may also include the 3D medical image(s) together with the target object detection results for the same.

The image processor 321 may execute the image processing program(s) 223 to implement a method for automatically detecting a target object from a 3D image.

In some embodiments, when executing the image processing program 223, the image processor 321 may associate the corresponding 3D images with the detection results, including the object classification and the detected bounding boxes, and transmit the 3D images together with (such as marked with) the detection results into the storage 322. Optionally, the memory 322 may communicate with the medical image database 325 to obtain images (with object(s) therein to be detected) therefrom or to transmit the 3D images together with the detection results to the medical image database 325.

In some embodiments, the 3D learning network may be stored in the memory 322. Optionally, the 3D learning network may be stored in a remote device, a separate database, such as the medical image database 325, distributed devices, and may be used by the image processing program(s) 223. The 3D images together with detection results may be stored as training samples in the medical image database 325.

The input/output 327 may be configured to allow the medical image processing device 300 to receive and/or send data. The input/output 327 may include one or more digital and/or analog communication devices that allow the device 300 to communicate with a user or other machine and device. For example, the input/output 327 may include a keyboard and a mouse that allow the user to provide an input.

The network interface 328 may include a network adapter, a cable connector, a serial connector, a USB connector, a parallel connector, a high-speed data transmission adapter such as optical fiber, USB 3.0, lightning, a wireless network adapter such as a WiFi adapter, a telecommunication (3G, 4G/LTE, etc.) adapters. The device 300 may be connected to the network through the network interface 328. The network may provide the functionality of local area network (LAN), a wireless network, a cloud computing environment (e.g., software as a service, platform as a service, infrastructure as a service, etc.), a client-server, a wide area network (WAN), and the like.

Besides displaying the medical images, the image display 329 may also display other information, such as the classification result and the detected bounding boxes. For example, the image display 329 may be an LCD, a CRT, or an LED display.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or non-recordable media (e.g., read-only memory (ROM), random access memory (RAM), disk storage media, optical storage media, flash memory devices, etc.).

As explained above, the 3D learning network according to the embodiments of present disclosure may work in an end-to-end manner, and predict the nodule class and bounding boxes directly. In some embodiments, to reduce computational and storage cost, a stage-wise training scheme may be used. The training scheme may be divided into three stages: (1) non-supervise learning; (2) small patch-based classification network training; and (3) large patch based detection network training. In some embodiments, stages (1) and (2) may be utilized to train the classification network (a part of the detection network), such as the base network disclosed herein, in order to produce a good network initialization for the whole detection network. In some embodiments, stage (3) may use an end-to-end training on large image patch.

In some embodiments, if the original 3D image is too large to be fitted into the image processor 321 (such modern GPU) memory, it may be split into a number of large patches according to the memory size of the image processor 321 so as to be fitted therein. By splitting the original 3D images into small patches and large patches and utilizing the stage-wise training scheme, including non-supervise training, training the classification network out of the 3D detection network on small patch, and then training the 3D detection network on the basis of the trained classification network, the total calculations needed for the training can be reduced substantially to be handled by a modern GPU.

Figure 5:
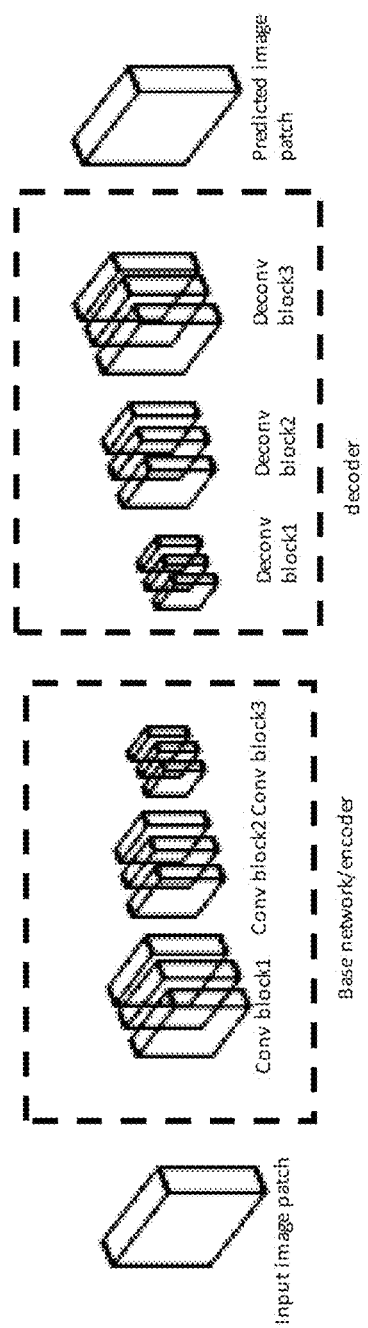
FIG. 5 illustrates a schematic illustration of the 3D learning network, according to an embodiment of present disclosure.

In an embodiment, the initial network weights may be generated using a 3D convolutional auto-encoder, as depicted in FIG. 5. In some embodiments, the encoder part is composed of cascaded convolutional blocks, for example, 3 convolution blocks, and the decoder part is composed of cascaded deconvolution blocks corresponding to the 3 convolutional blocks of the encoder part. Within the deconvolution blocks, the deconvolution layer(s) are composed of up-sampling layer(s) followed by convolution layer(s). As shown in FIG. 5, an image patch is input, on which convolution operations are performed by the encoder part and deconvolution operations are performed by the decoder part, and then the predicted image patch is output. The 3D convolutional auto-encoder may be trained so that the output image patch is the same as the input image patch (the target image patch). In an embodiment, noise, such as Gaussian noise, may be added to the input image patch but not into the target output image patch, so as to make the learning robust. In some embodiments, both the input image patch and the target output image patch may be transformed, such as rotated, distorted, scaled up/down, etc., to make the learning more robust. Then, the network weights of the trained encoder (i.e., the base network) are utilized to initialize the supervised training procedure.

Figure 6:
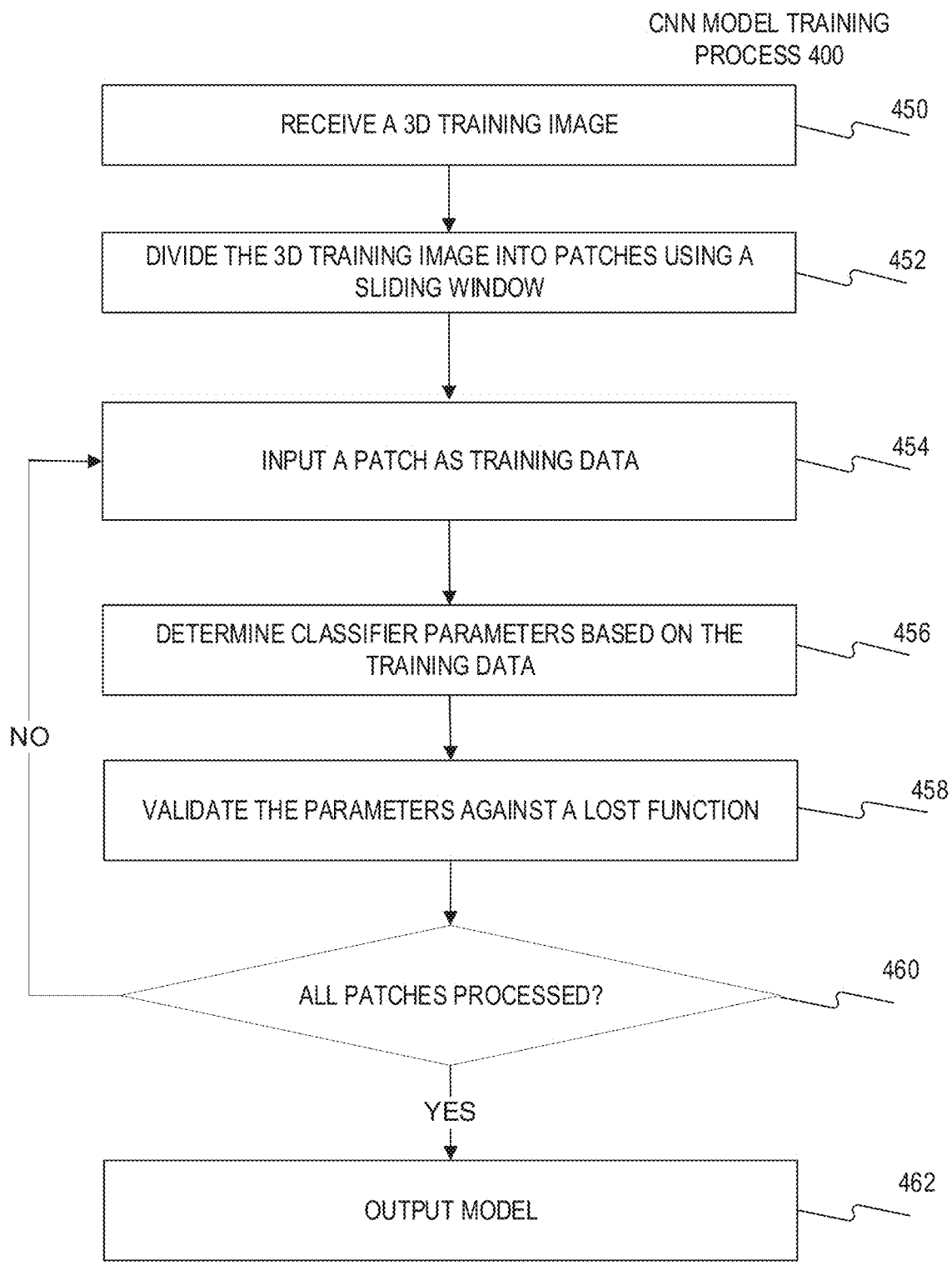
FIG. 6 illustrates a flow chart of an exemplary process for training convolutional neutron network model, according to an embodiment of present disclosure.

The detection network includes the classification network. In one embodiment, the classification network may be trained before training the detection network. FIG. 6 illustrates a flow chart of the convolutional neutron network training process 400 for training the classification network therein. The process 400 starts at the step 450 of receiving a 3D training image and associated classification result. In some embodiments, the 3D training image may be divided into patches, for example using a sliding window, at step 452. Then, at step 454, a single patch together with the classification result thereof are input into the classification network as training data. In some embodiments, the weights of the classification network may have been initialized. At step 456, the classifier parameters of the classification network may be determined based on the training data. The determination of classifier parameters may involve validating against a lost function, at step 458. In some embodiments, steps 456 and 458 may also be integrated in the same step, wherein the classifier parameters of the classification network may be optimized against a lost function on the basis of each patch. In some embodiments, the optimization process may be performed by any one of the common algorithms, including but not limited to the gradient descent algorithm, Newton's method, conjugate gradient algorithm, quasi Newton method, and Levenberg Marquardt algorithm, etc. At step 460, it determines whether all patches are already processed, if so, then at step 462, the trained classification network with present optimized classifier parameters is output as the trained model. Otherwise, the process returns to step 454 to process a subsequent patch, until all the patches are processed. At Step 452, the 3D training image may be divided into patches using a sliding window. In an embodiment, the last fully connected layers of the convolution network as the classification network (or the detection network) may be converted to fully convolution layers as explained above by referring to FIG. 3. A stride of the convolution operation acts like a stride of a sliding window and these operations are equivalent. Due to fast convolution computation on a GPU, a huge speed-up is gained.

In some embodiments, based on the trained classification network, the detection network may be constructed and trained on large patches. For example, the training process 400 for the classification network may be adapted to train the detection network. The differences are as follows: the training data input at step 454 are a large patch and information on the detected bounding boxes therein as containing a target object, such as a set of parameters identifying the corresponding detected bounding boxes. Such set of parameters may include but not limit to a label (associated with the target object in the large patch) and a set of location parameters of the detected bounding boxes. As an example, a Label 0 may represent that the 3D image patch does not contain nodule (i.e., the detected bounding box therein contains the non-nodule target object), and Labels 1-9 may represent that the 3D image patch contains a nodule of different Sizes 1-9, respectively (i.e., the detected bounding box therein contains the Size n-nodule target object, n is a integer in the range of 1-9). The differences also exist in steps 456 and 458, wherein the parameters to be optimized against the lost function are those belongs to the detection network.

In some embodiments, for training the detection network, a label may be assigned to each anchor box. In an embodiment, if the anchor box(es) has an intersection-over-union (IoU) overlap higher than a certain threshold (e.g. 0.7) with any ground-truth box, then a label corresponding to the ground-truth box may be assigned to the anchor box(es). Note that a single ground-truth box (e.g. tight bounding box containing a nodule) may assign a corresponding label to multiple anchor boxes. For example, a non-nodule inside lung label may be assigned to a non-nodule anchor box if its IoU ratio is lower than 0.3 for all ground-truth boxes outside lungs. In contrast, a non-nodule outside lung label may be assigned to a non-nodule anchor box if its IoU ratio is lower than 0.3 for all ground-truth boxes inside lungs.

In an embodiment, the loss function for training the detection network may be a multi-task loss function, to cover both the classification task and the bounding box prediction task. For example, the multi-task loss function may be defined by formula (3).

$$L(\{p_i\}, \{t_i\}) = \frac{1}{N_{cls}} \sum_i L_{cls}(p_i, p_i^*) + \lambda \frac{1}{N_{reg}} \sum_i L_{reg}(t_i, t_i^*) \quad \text{formula (3)}$$

Where i is the index of an anchor box in a training mini-batch and $p_i$ is the predicted probability of anchor box i being nodule. The ground-truth label is $p_i^*$, $t_i$ represents the 6 parameterized coordinates of the predicted bounding box, and $t_i^*$ is that of the ground-truth box associated with a nodule anchor box. $L_{cls}$ is cross-entropy loss, and $L_{reg}$ is the robust loss function. In some embodiments, $N_{cls}$ and $N_{reg}$ may be the numbers of bounding boxes in the mini-batch and are used for normalization, respectively. $\lambda$ is a weighting parameter between classification task and regression task.

As an example, a 6-parameter regression may be adopted for a bounding box regression, and the 6 parameters may be defined by formula (4).

$$dx = \frac{x - x_a}{w_a}, dy = \frac{y - y_a}{h_a}, dz = \frac{z - z_a}{d_a}, \quad \text{formula (4)}$$

$$dsize_x = \log\left(\frac{w}{w_a}\right), dsize_y = \log\left(\frac{h}{h_a}\right), dsize_z = \log\left(\frac{d}{d_a}\right),$$

$$dx^* = \frac{x^* - x_a}{w_a}, dy^* = \frac{y^* - y_a}{h_a}, dz^* = \frac{z^* - z_a}{d_a},$$

$$dsize_x^* = \log\left(\frac{w^*}{w_a}\right), dsize_y^* = \log\left(\frac{h^*}{h_a}\right), dsize_z^* = \log\left(\frac{d^*}{d_a}\right)$$

Where x, y, z, w, h, and d denote the bounding box's center coordinates and its width, height and depth. Variables x, $x_a$, and x* are for the predicted bounding box, anchor box and ground-truth box respectively (likewise for y, z, w, h and d).

Figure 7:
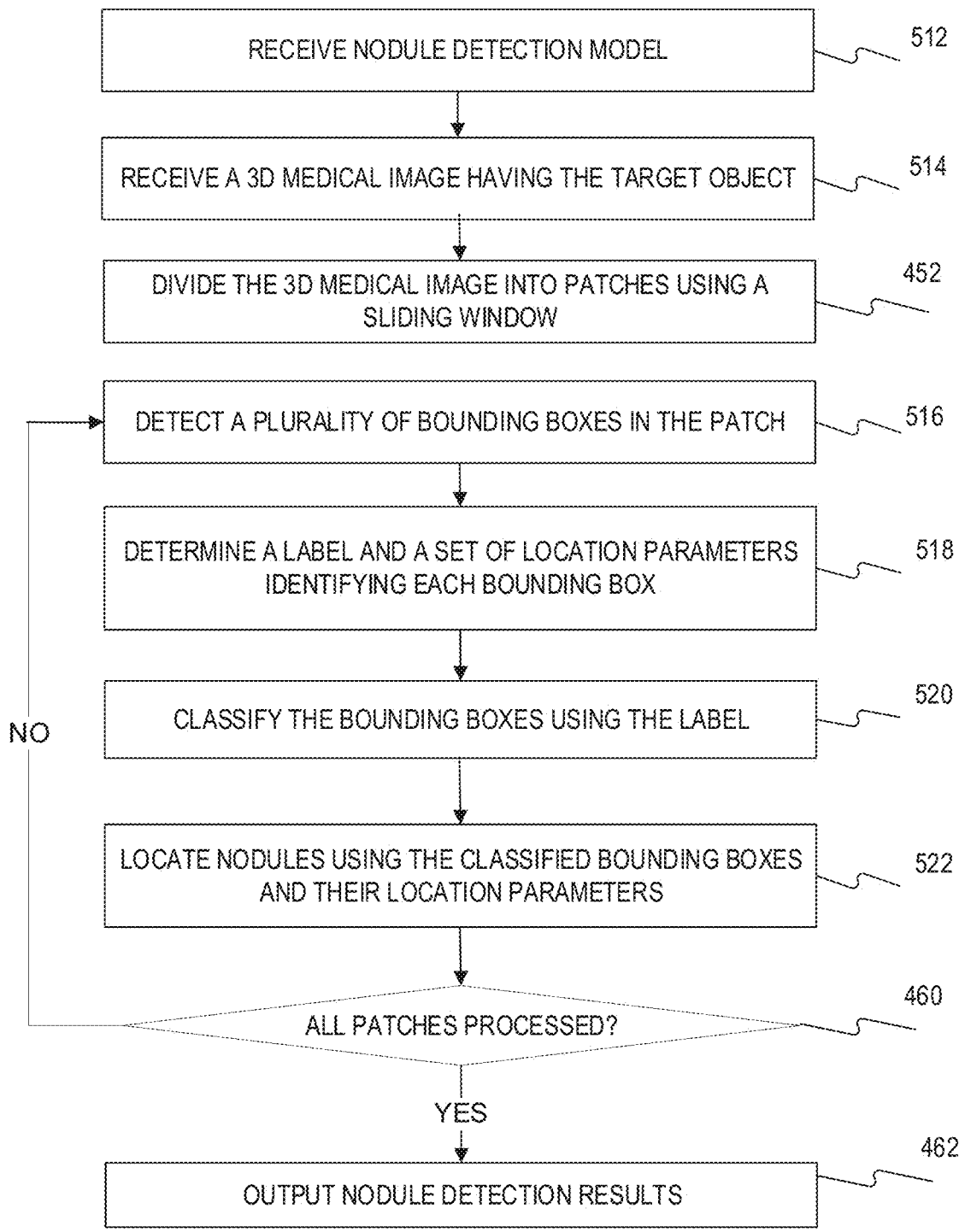
FIG. 7 illustrates a flow chart of an exemplary process for identifying the target object, according to an embodiment of present disclosure.

FIG. 7 illustrates a flow chart of an exemplary process 500 for identifying the target object in the 3D image scan. The target object identification process 500 starts at step 512, wherein the trained nodule detection model is received. At step 514, a 3D medical image that may include a target object is received. Then, the 3D medical image may be divided into patches using a sliding window at step 452. At step 516, a plurality of bounding boxes are detected from the patch using the detection network. At step 518, a label and a set of location parameters identifying each bounding box is determined. As an option, steps 516 and 518 may be integrated in the same step. Then, the bounding boxes may be classified using the label at step 520, and the target objects, such as the nodules, may be located using the classified bounding boxes and their location parameters. At step 460, it is determined whether all the patches are processed, if so, the nodule detection results of each patch are integrated to obtain and output the complete nodule detection result at step 462. If not, then the process 500 returns to step 516. Although the target object identification process 500 as shown in FIG. 7 is based on sliding window, but it is not limited thereto. In an embodiment, the last fully connected layers of the convolution network as the classification network (or the detection network) may be converted to fully convolution layers as explained above by referring to FIG. 3. A stride of the convolution operation acts like a stride of a sliding window and these operations are equivalent. Due to fast convolution computation on a GPU, a huge speed-up is gained.

Figure 8:
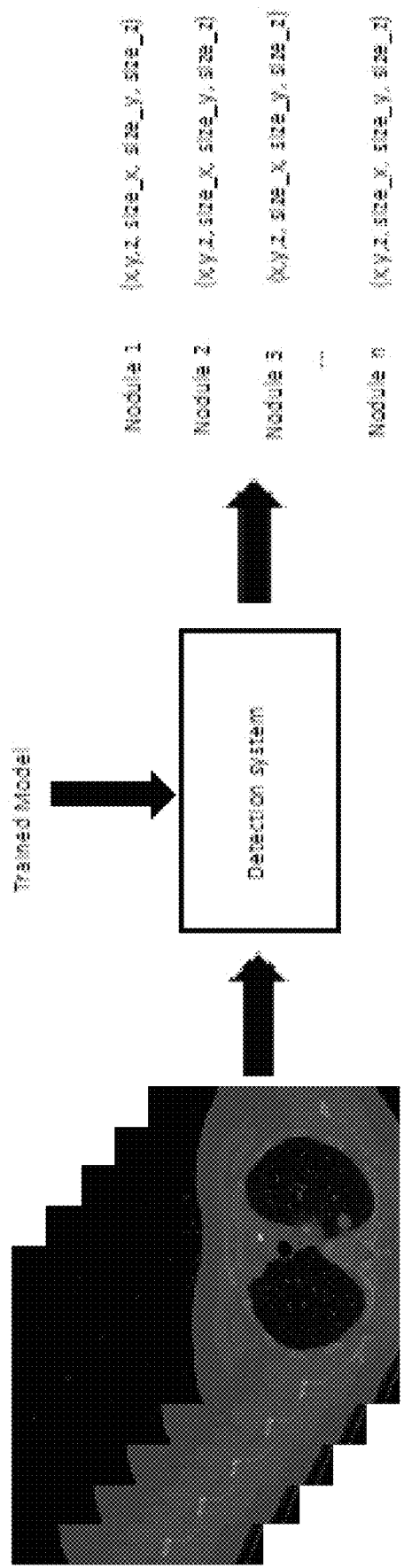
FIG. 8 illustrates an exemplary process for automatically detecting a target object from a 3D image, according to an embodiment of present disclosure.

FIG. 8 illustrates an exemplary process for automatically detecting a target object from a 3D image according to another embodiment of present disclosure. As shown in FIG. 8, the 3D pulmonary volumetric CT images may be input into the detection system, which detects the nodules therein using the trained model, and identifies the corresponding bounding box containing each of the nodules, including the position and the size of the corresponding bounding box.

In some embodiments, the 3D image may be divided along various directions, such as but not limited to z direction, into smaller chunks, then the detection network and its associated algorithm may be applied to each chunk to get the corresponding detection result of the target object. The detection result of each chunk may be collected and the chunks with the corresponding detection results may be integrated to yield the complete detection results for the entire 3D image.

Figure 9:
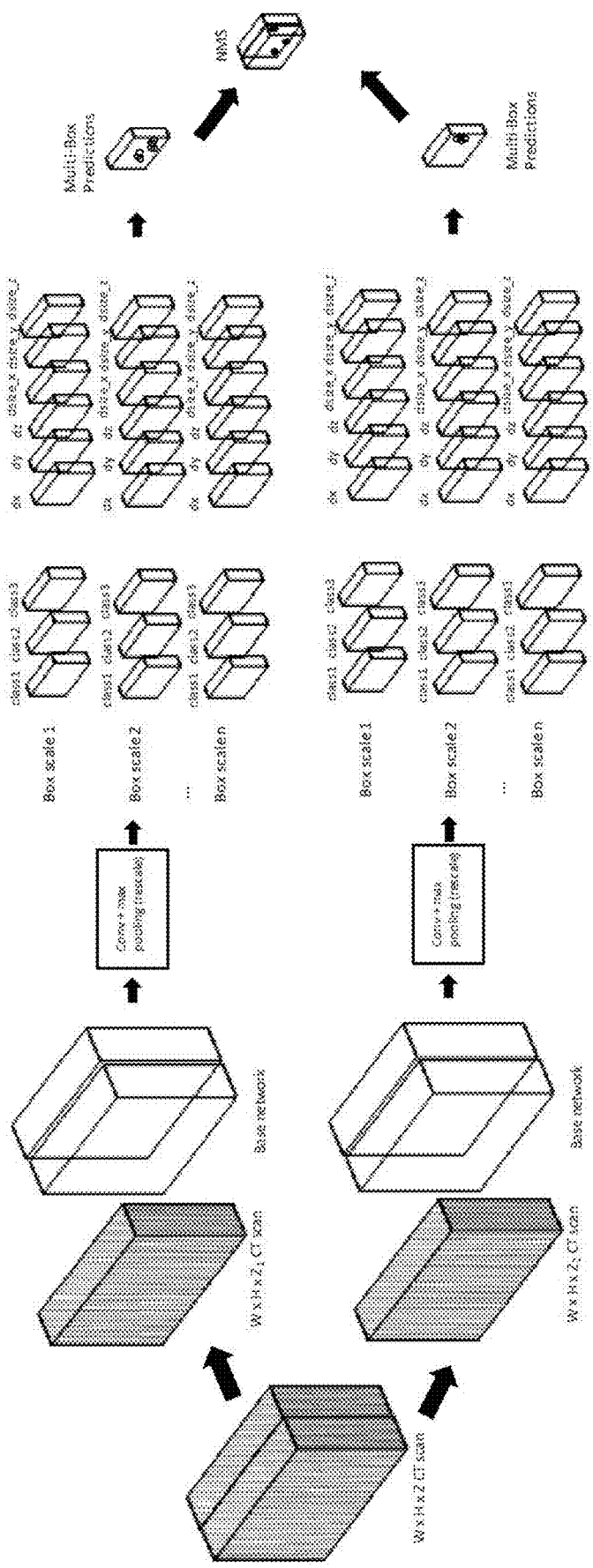
FIG. 9 illustrates an exemplary nodule detecting process using a 3D learning network of n scales, according to an embodiment of present disclosure.

FIG. 9 illustrates an exemplary nodule detecting process using a 3D learning network of n scales. As shown by FIG. 9, the input 3D medical image is a W*H*Z volumetric CT scan. In order to fit the detection network and feature maps into GPU memory, the input CT scan is divided into smaller chunks, note that FIG. 9 illustrates two chunks, W*H*$Z_1$ CT scan and W*H*$Z_2$ CT scan, as an example to clarify and exemplify the detecting process, actually the number of chunks may be chosen as needed, so as to fit the performance of the GPU. For example, the base network corresponds to scale 1, and the learning network corresponding to other scales, including scales 2~n, may be implemented by rescaling operation on the base network, including but not limited to convolution and max pooling. Each chunk may have 3 class labels for the bounding box. The bounding box(es) within each chunk may be detected using the feature maps of the 3 classes of various scales. The detection may include the class label of the bounding box and regressed 6 offset parameters (dx, dy, dz, dsize_x, dsize_y, and dsize_z) from the anchor box. The detected bounding boxes for all the chunks, i.e., the multi-box predictions as shown in FIG. 9, may be combined and transformed into original image coordinate system, followed by a 3D non-maximal suppression, to get the final detection result. By means of the 3D non-maximal suppression, the redundant bounding box(es) may be cancelled, to simplify and clarify the detection/ location results of the target objects in the 3D medical image. For example, as a result of the 3D non-maximal suppression, one detected bounding box may be determined for one nodule.

Optionally, segmentation may be performed before running the detection algorithm to constrain the detection algorithm to a potential region of the 3D medical image instead of the whole 3D medical image. Accordingly, the detection accuracy may be improved while the calculation amount needed for the detection network may be reduced.

Taking a lung nodule as an example of the target object, it is known that lung nodules are always inside the lung. In an embodiment, lung segmentation may be performed in advance to further remove false alarms inside the lung. Particularly, lung segmentation may be performed in advance to generate lung convex hull and then utilize the convex hull to constrain nodule detection. Lung segmentation may be performed by various means, including but not limited to convolutional networks, active contour model, watershed segmentation algorithm, etc. In some embodiments, such lung segmentation may be performed in a lower resolution scan and the result may be up-sampled to the original resolution, to fit the 3D learning network and feature maps to a GPU memory while speeding up the segmentation procedure.

In a clinical setting, radiologists usually need to perform quantitative analysis of the lung nodules. For example, besides the detected bounding box, they also need the boundary of nodules, and the accurate sizes of the detected nodules, etc., which depend on the nodule segmentation. In some embodiments, the segmentation may be performed on the basis of the detected bounding box. For example, segmentation may be performed inside the detected bounding box of lung nodule using 3D convolutional network. Accordingly, the segmentation model/learning network may be trained on smaller nodule patches and applied to the image region inside the detected bounding box.

Figure 10:
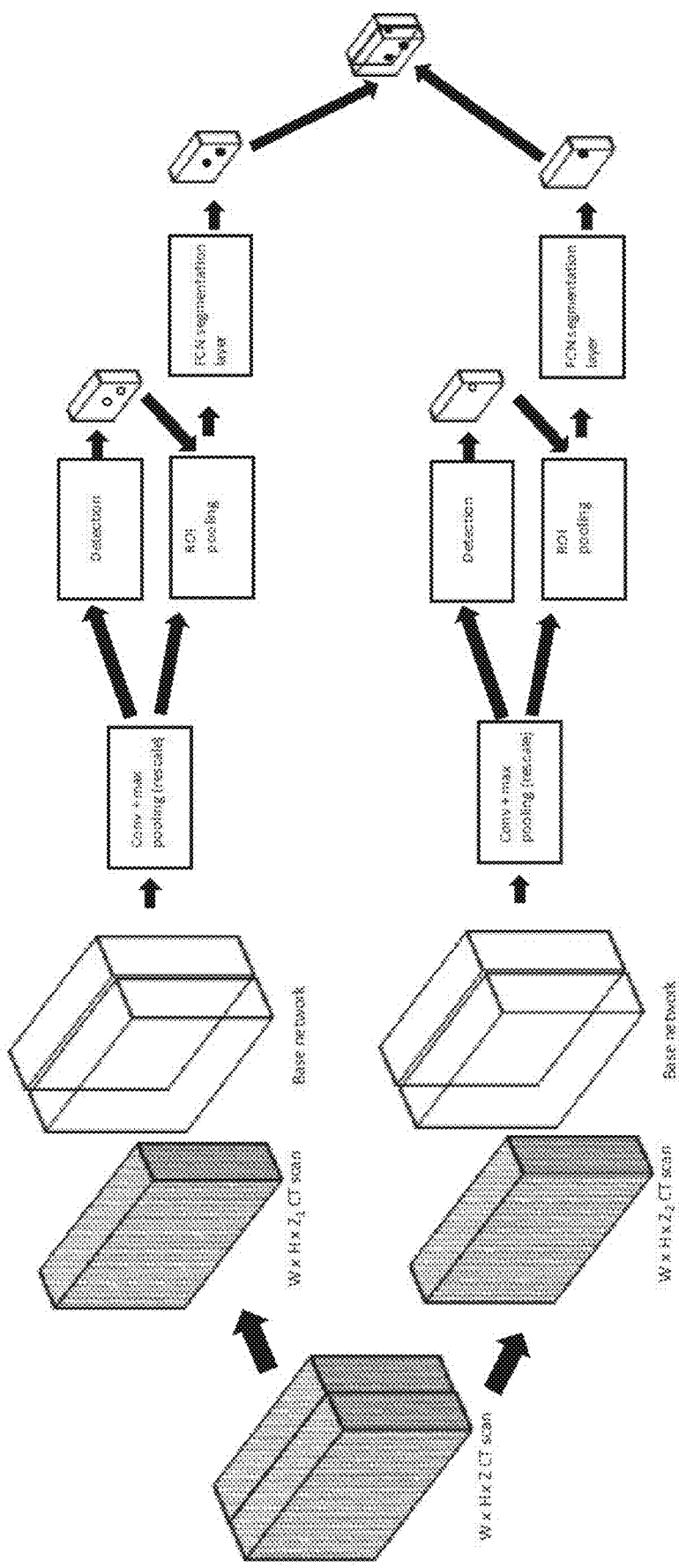
FIG. 10 illustrates an exemplary nodule segmenting process using a 3D learning network of one scale, according to an embodiment of present disclosure.

In one embodiment, the nodule segmentation and detection may be integrated into a nodule segmenting process, as illustrated by FIG. 10, to realize an end-to-end detection and segmentation process. Although in FIG. 10, the input W*H*Z 3D scan is divided into two CT scans, it is contemplated that the input 3D scan may be divided into any suitable number of CT scans. For each divided CT scan, various rescaling operations, including convolution and max pooling operations, may be performed on the base network to get the detection result on the corresponding scale. Once the bounding box are detected, the bounding box may be scaled back to the feature map space (e.g. re-aligned back to the last feature layers) and then a ROI (region of interest) pooling is applied thereon, resulting in ROI regions. Segmentation algorithm may be performed on each ROI to directly generate nodule segmentation. Such segmentation algorithm may be implemented by a FCN segmentation layer as an example. Such segmentation algorithm may also be implemented by a series of deconvolution layers or up-sampling layers following convolution layers. In some embodiments, nodule segmentation results of each divided CT scan may be integrated, to obtain the whole nodule segmentation result in the input original CT scan. In an embodiment, the pooling uses bilinear interpolation and resampling to make the ROIs the same size, to speed up the GPU calculations.

It is contemplated that the nodule segmenting process as shown by FIG. 10 may be extended from the previous detection network, where the detection and segmentation stages may share the same detection network, for example, the base network.

In some embodiments, the training for the network used in FIG. 10 may be performed as follows. Firstly, the detection network is trained to obtain the weights of the detection network part. Then, given the weights of the detection network part, the segmentation network part is trained using ground truth bounding box. Several loss functions may be adopted for training the segmentation network part, including but not limited to normalized cross-entropy based on foreground and background voxel number. The above two networks may be combined to obtain the nodule segmentation result.

The detection network part and the segmentation network part may be trained separately, subsequently, or simultaneously. In one embodiment, during the training stage, both the detection network part and the segmentation network part may be trained at the same time against a joint loss function, with ground truth bounding box and segmentation as a supervision for the segmentation. And the joint loss function may be defined by formula (5).

$$L(\{p_i\}, \{t_i\}, \{s_j\}) = \frac{1}{N_{cls}} \sum_i L_{cls}(p_i, p_i^*) + \lambda \frac{1}{N_{reg}} \sum_i L_{reg}(t_i, t_i^*) + \eta \frac{1}{N_{seg}} \sum_j L_{seg}(S_j, S_j^*) \quad \text{formula (5)}$$

where the former terms are the same as those in formula (3) and thus omit its definition. The last term is the loss component of the segmentation. $N_{seg}$ is the number of segmentation regions in one mini-batch. $L_{seg}$ is voxel-wise loss function across one region, j is the index of a region of interest in a training mini-batch and $S_j$ is the predicted probability of region of interest and $S_j^*$ is ground truth segmentation.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Exemplary Methods described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for automatically detecting a target object from a 3D image using a 3D learning network comprising a segmentation network part and a detection network part, comprising:
    receiving the 3D image acquired by an imaging device;
    segmenting, by a processor, the 3D image using the segmentation network part of the 3D learning network to obtain a potential region;
    detecting, by the processor, a plurality of bounding boxes as containing the target object using the detection network part of the 3D learning network, wherein the detecting the plurality of bounding boxes is constrained by the potential region, wherein the 3D learning network is trained to generate a plurality of feature maps of varying scales based on the 3D image, wherein the detection network part and the segmentation network part are trained at the same time against a joint loss function, wherein the plurality of feature maps are generated respectively corresponding to a plurality of different sizes of the target object;
    determining, by the processor, a set of parameters identifying each detected bounding box using the 3D learning network;
    segmenting, by the processor using the segmentation network part, the target object within the plurality of bounding boxes detected by the detection network part, wherein the segmenting the 3D image to obtain the potential region is performed at a first resolution and the detecting the plurality of bounding boxes is performed at a second resolution higher than the first resolution; and
    locating, by the processor, the target object based on the set of parameters.

2. The computer-implemented method of claim 1, wherein the set of parameters include coordinates identifying a position of each bounding box in the 3D image.

3. The computer-implemented method of claim 1, wherein the set of parameters include dimensions identifying a size of each bounding box.

4. The computer-implemented method of claim 1, wherein the 3D learning network is trained to perform a regression on the set of parameters.

5. The computer-implemented method of claim 1, further comprising associating a plurality of anchor boxes with the 3D image, wherein the set of parameters are indicative of offsets of each bounding box relative to a respective anchor box.

6. The computer-implemented method of claim 5, wherein each anchor box is associated with a grid cell of a feature map.

7. The computer-implemented method of claim 6, wherein each anchor box is scaled according to the scale of the feature map.

8. The computer-implemented method of claim 1, wherein the plurality of feature maps have varying image sizes.

9. The computer-implemented method of claim 1, wherein the plurality of feature maps use varying sized sliding windows.

10. The computer-implemented method of claim 1, further comprising creating initial bounding boxes, wherein detecting the plurality of bounding boxes as containing the target object includes classifying the initial bounding boxes to be associated with a plurality of labels.

11. The computer-implemented method of claim 10, wherein the plurality of labels comprise labels indicative of a given size from the plurality of different sizes of the target object.

12. The computer-implemented method of claim 1, further comprising applying a non-maximum suppression to the detected plurality of bounding boxes.

13. The computer-implemented method of claim 1, wherein the imaging device is a computed tomography imaging system.

14. The computer-implemented method of claim 1, wherein the target object is a lung nodule.

15. The computer-implemented method of claim 1, wherein the 3D learning network is a fully convolutional neural network.

16. A system for automatically detecting a target object from a 3D image using a 3D learning network comprising a segmentation network part and a detection network part, comprising:
  an interface configured to receive the 3D image acquired by an imaging device; and
  a processor configured to:
    segment the 3D image using the segmentation network part of the 3D learning network to obtain a potential region;
    detect a plurality of bounding boxes as containing the target object using the detection network part of the 3D learning network, wherein the detection of the plurality of bounding boxes is constrained by the potential region, wherein the 3D learning network is trained to generate a plurality of feature maps of varying scales based on the 3D image, wherein the detection network part and the segmentation network part are trained at the same time against a joint loss function, wherein the plurality of feature maps are generated respectively corresponding to a plurality of different sizes of the target object;
    determine a set of parameters identifying each detected bounding box using the 3D learning network;
    segment, using the segmentation network part, the target object within the plurality of bounding boxes detected by the detection network part, wherein the 3D image is segmented to obtain the potential region at a first resolution and the plurality of bounding boxes is detected at a second resolution higher than the first resolution; and
  locate the target object based on the set of parameters.

17. The system of claim 16, wherein the processor includes a Graphic Processing Unit (GPU).

18. The system of claim 16, wherein the imaging device is a computed tomography imaging system.

19. A non-transitory computer readable medium having instructions stored thereon, wherein the instructions, when executed by a processor, perform a method for automatically detecting a target object from a 3D image using a 3D learning network comprising a segmentation network part and a detection network part, the method comprising:
  receiving the 3D image acquired by an imaging device;
  segmenting the 3D image using the segmentation network part of the 3D learning network to obtain a potential region;
  detecting a plurality of bounding boxes as containing the target object using the detection network part of the 3D learning network, wherein the detecting the plurality of bounding boxes is constrained by the potential region, wherein the 3D learning network is trained to generate a plurality of feature maps of varying scales based on the 3D image, wherein the detection network part and the segmentation network part are trained at the same time against a joint loss function, wherein the plurality of feature maps are generated respectively corresponding to a plurality of different sizes of the target object;
  determining a set of parameters identifying each detected bounding box using the 3D learning network;
  segmenting, using the segmentation network part, the target object within the plurality of bounding boxes detected by the detection network part, wherein the segmenting the 3D image to obtain the potential region is performed at a first resolution and the detecting the plurality of bounding boxes is performed at a second resolution higher than the first resolution; and
  locating the target object based on the set of parameters.

20. The non-transitory computer readable medium of claim 19, the method further comprising creating initial bounding boxes, wherein detecting the plurality of bounding boxes as containing the target object includes classifying the initial bounding boxes to be associated with a plurality of labels, wherein the plurality of labels comprise labels indicative of a given size from the plurality of different sizes of the target object.

* * * * *